United States Patent
Samuelsson (10) Patent No.: US 8,854,122 B2
(45) Date of Patent: Oct. 7, 2014

(54) ACTIVE INTERFERENCE-NOISE CANCELLATION DEVICE, AND A METHOD IN RELATION THERETO

(71) Applicant: St. Jude Medical Systems AB, Uppsala (SE)

(72) Inventor: Magnus Samuelsson, Uppsala (SE)

(73) Assignee: St. Jude Medical Systems AB, Uppsala (SE)

( * ) Notice: Subject to any disclaimer, the term of this patent is extended or adjusted under 35 U.S.C. 154(b) by 21 days.

(21) Appl. No.: 13/693,895

(22) Filed: Dec. 4, 2012

(65) Prior Publication Data

US 2013/0342268 A1 Dec. 26, 2013

Related U.S. Application Data

(60) Provisional application No. 61/630,097, filed on Dec. 5, 2011.

(30) Foreign Application Priority Data

Dec. 5, 2011 (SE) ...................................... 1151152

(51) Int. Cl.
| | | |
|---|---|---|
| H03B 1/00 | (2006.01) | |
| H03H 11/12 | (2006.01) | |
| A61B 5/0215 | (2006.01) | |
| A61B 5/01 | (2006.01) | |
| A61B 5/026 | (2006.01) | |
| A61B 5/06 | (2006.01) | |
| A61B 5/00 | (2006.01) | |
| A61B 5/145 | (2006.01) | |

(52) U.S. Cl.
CPC ........ *H03H 11/12* (2013.01); *A61B 5/01* (2013.01); *A61B 5/026* (2013.01); *A61B 5/065* (2013.01); *A61B 5/6851* (2013.01); *A61B 5/14539* (2013.01); *A61B 5/7203* (2013.01); *A61B 5/0215* (2013.01)
USPC ............................................ 327/552; 327/561

(58) Field of Classification Search
USPC ......... 327/551, 552, 558, 559, 560, 561, 562, 327/563
See application file for complete search history.

(56) References Cited

U.S. PATENT DOCUMENTS

| 4,243,044 A | 1/1981 | Blancke |
|---|---|---|
| 4,890,630 A | 1/1990 | Kroll et al. |

(Continued)

FOREIGN PATENT DOCUMENTS

WO WO 2011/062683 A1 5/2011

OTHER PUBLICATIONS

A. C. Mettingvanrijn et al., "Amplifiers for bioelectric events: a design with a minimal number of parts", Medical and Biological Engineering and Computing, Springer, Heildelberg, Germany, vol. 32, No. 3, May 1, 1994, pp. 305-310.

(Continued)

*Primary Examiner* — Jeffrey Zweizig
(74) *Attorney, Agent, or Firm* — Foley & Lardner LLP (57) ABSTRACT

An active noise cancellation device (2) for a medical device includes an active circuit having a first input connection (8), a second input connection (10), and an output connection (12). The second input connection (10) is connected to at least one predetermined reference signal. The active noise cancellation device (2) further includes a low-impedance body connection electrode (4) adapted to be in electrical contact with a bloodstream of a subject, wherein the low-impedance body connection electrode (4) is connected to said first input connection (8), and a feedback branch (14) connecting the output connection (12) with the first input connection (8). The feedback branch (14) comprises a current limiting circuit (18) to limit a current through said feedback branch (14) to be lower than a predetermined current.

26 Claims, 4 Drawing Sheets

(56) References Cited

U.S. PATENT DOCUMENTS

| | | |
|---|---|---|
| 5,392,784 A | 2/1995 | Gudaitis |
| 6,112,598 A | 9/2000 | Tenerz et al. |
| 6,584,351 B1 | 6/2003 | Ekwall |
| 7,207,227 B2 | 4/2007 | Rangsten et al. |
| 7,326,088 B2 | 2/2008 | Tulkki |
| 7,724,148 B2 | 5/2010 | Samuelsson et al. |
| 7,794,658 B2 * | 9/2010 | Kermani et al. ............ 422/82.01 |
| 7,909,768 B1 * | 3/2011 | Turcott ........................ 600/481 |
| 8,010,174 B2 * | 8/2011 | Goode et al. .................. 600/347 |
| 2005/0043598 A1 | 2/2005 | Goode, Jr. et al. |
| 2006/0009817 A1 | 1/2006 | Tulkki |
| 2006/0099834 A1 | 5/2006 | Tulkki |
| 2007/0004988 A1 | 1/2007 | Wu et al. |
| 2008/0039904 A1 | 2/2008 | Bulkes et al. |
| 2008/0139953 A1 | 6/2008 | Baker et al. |
| 2008/0183098 A1 | 7/2008 | Denison et al. |
| 2008/0275531 A1 | 11/2008 | Bulkes et al. |
| 2009/0120810 A1 | 5/2009 | Phan et al. |
| 2009/0275838 A1 | 11/2009 | Marshall et al. |
| 2010/0113964 A1 | 5/2010 | Wahlstrand et al. |
| 2011/0021943 A1 | 1/2011 | Lacour et al. |
| 2011/0193633 A1 | 8/2011 | Yoon et al. |
| 2011/0201906 A1 | 8/2011 | Samuelsson |

OTHER PUBLICATIONS

R. A. Blum et al., "An Integrated System for Simultaneous, Multichannel Neuronal Stimulation and Recording", IEEE Transactions on Circuits and Systems, vol. 54, No. 12, Dec. 2007, pp. 2608-2618.

* cited by examiner

(Prior Art)

FIG. 1

(Prior Art)

FIG. 2

(Prior Art)

ACTIVE INTERFERENCE-NOISE CANCELLATION DEVICE, AND A METHOD IN RELATION THERETO

CROSS-REFERENCE TO RELATED PATENT APPLICATIONS

This application claims priority from U.S. Provisional Application No. 61/630,097, filed Dec. 5, 2011, incorporated herein by reference in its entirety.

BACKGROUND

The present invention relates to a device and method for active noise cancellation applicable to medical intra-body sensors.

In many medical procedures, various physiological conditions present within a body cavity need to be monitored. These physiological conditions are typically physical in nature—such as pressure, temperature, rate-of-fluid flow, and provide the physician or medical technician with critical information as to the status of a patient's condition.

One device that is widely used to monitor conditions is the blood pressure sensor. A blood pressure sensor senses the magnitude of a patient's blood pressure, and converts it into a representative electrical signal that is transmitted to the exterior of the patient.

In the prior art, it is known to mount a sensor at a distal portion of a so-called sensor wire and to position the sensor by using the sensor wire in a blood vessel in a living body to detect a physical parameter, such as pressure or temperature. The sensor includes elements that are directly or indirectly sensitive to the parameter.

One known sensor wire has a typical length of 1.5-2 meters, and comprises a hollow tubing running along a major part of the wire and having an outer diameter in the range of 0.25-0.5 mm, typically approximately 0.35 mm. A core wire is arranged within the tubing and extends along the tubing and often extends out from a distal opening of the tubing. The sensor or sensors is/are preferably arranged in connection with the distal portion of the core wire, e.g. at the distal end of the sensor wire.

The present invention is applicable, for example, in relation with a sensor wire of the type described above.

In one application the sensor wire of the type described above is used to measure pressure in blood vessels, and in particular in the coronary vessels of the heart, e.g. to identify constrictions in the coronary vessels. This may be performed by determining the so-called Fractional Flow Reserve related to the vessel. The sensor wire is typically inserted by use of an insertion catheter, which in turn is inserted via the femoral vein or the radial artery, and guided by the inserted catheter to the measurement site.

In order to power the sensor and to communicate signals representing the measured physiological variable to an external physiology monitor, one or more cables or leads, often denoted microcables, for transmitting the signals are connected to the sensor, and are routed along the sensor wire to be passed out from the vessel to the external physiology monitor, via physical cables or wirelessly.

The sensor element further comprises an electrical circuitry, which generally is connected in a Wheatstone bridge-type of arrangement to one or several piezoresistive elements provided on a membrane. As is well known in the art, a certain pressure exerted on the membrane from the surrounding medium will thereby correspond to a certain stretching or deflection of the membrane and thereby to a certain resistance of the piezoresistive elements mounted thereon and, in turn, to a certain output from the sensor element.

In U.S. 2006/0009817 A1, which is incorporated herein in its entirety for the medical devices and methods disclosed within, and which is assigned to the present assignee, an example of such a sensor and guide wire assembly is disclosed. The system comprises a sensor arranged to be disposed in the body, a control unit arranged to be disposed outside the body and a wired connection between the sensor and the control unit, to provide a supply voltage from the control unit to the sensor and to communicate a signal there between. The control unit further has a modulator, for modulating the received sensor signal and a communication interface for wireless communication of the modulated signal.

In U.S. Pat. No. 7,724,148 B2, which is incorporated herein in its entirety for the medical devices and methods disclosed within, and which also is assigned to the present assignee, another example of such pressure measurement system is disclosed. The pressure sensor wire is adapted to be connected, at its proximal end, to a transceiver unit that is adapted to wirelessly communicate via a communication signal with a communication unit arranged in connection with an external device.

In U.S. Pat. No. 6,112,598, which is incorporated herein in its entirety for the medical devices and methods disclosed within, and assigned to the present assignee, and also in U.S. Pat. No. 7,207,227 B2, which is incorporated herein in its entirety for the medical devices and methods disclosed within, further examples of such pressure sensors and guide wire assemblies are disclosed.

In U.S. Pat. No. 7,326,088, which is incorporated herein in its entirety for the medical devices and methods disclosed within, and assigned to the present assignee, a device adapted for reducing leaking current in a guide wire assembly is disclosed. In this known device a guard potential is applied to an insulator or to a conductive guide wire sheath of the guide wire assembly in order to thereby reduce current leakage.

Figure 1:
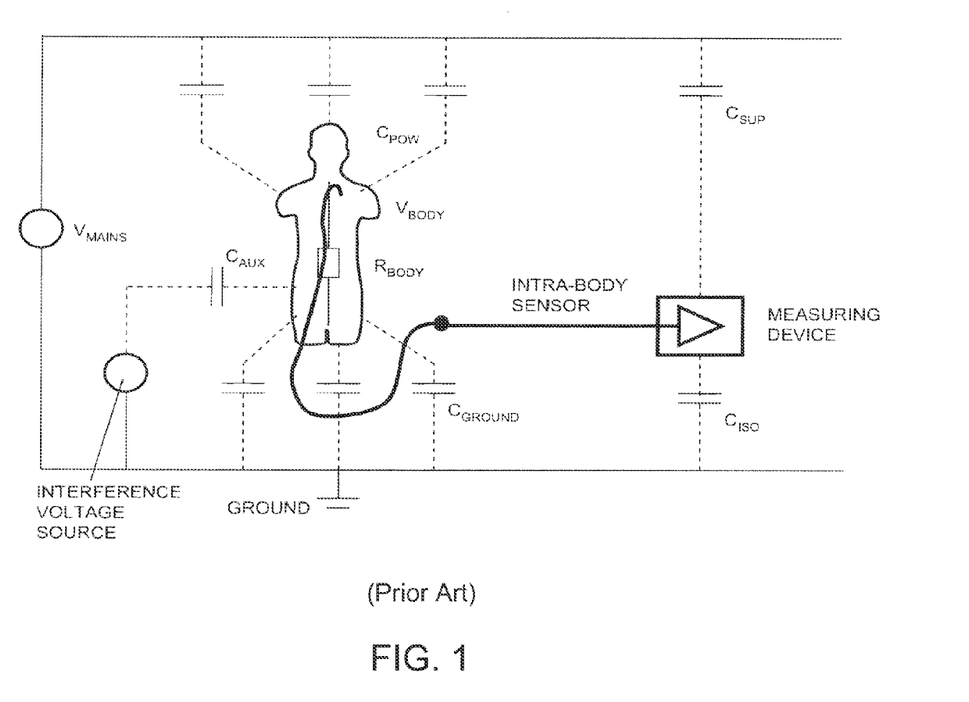
FIG. 1 is a simplified illustration of how external environmental voltages influence the patient body.

The patient body acts as an electrically conductive volume with a large surface area exposed to surrounding electrical equipment (fluorescent lighting, X-ray power supplies, etc.) as well as a direct conduction path to intra-body electrical devices (pacemakers, neurostimulators, RF ablation devices, ultrasound catheters, etc.). The man-made electrical interference noise created by such equipment thus efficiently couples onto the patient body through capacitive coupling in the case of external equipment and directly through conduction and/or capacitive coupling in the case of intra-body equipment. This is problematic for precision electrical intra-body sensors since interference voltages many thousand times larger than the signals of interest may corrupt the measurements. A simplified illustration of the influence onto the patient body is illustrated in FIG. 1. In FIG. 1, different influencing capacitances are indicated. For example, Cground (e.g., 300 pF) is the capacitance to ground, Cpow (e.g., 3 pF) is the capacitance in relation to the main power supply, and Csup, Ciso are capacitances in relation to a measuring device connected to the body via an intra-body sensor. Furthermore, the main supply Vmain is an alternating (50/60 Hz) voltage of 230 Volt, for example. Rbody is the resistance of the body and may be approximated to 100Ω. This may result in a voltage Vbody across the body of about 2.3 VAC having a frequency of 50 Hz. This voltage Vbody may naturally influence the measurements performed, for example, by an intra-body sensor being a pressure sensor of the kind described above.

Direct electrical shielding of intra-body sensors is not always possible due to potentially life-threatening electrical leakage current situations that may develop due to sensor mechanical failure. Such a mechanical failure is considered a single-mode fault condition (SFC). In accordance with applicable safety standards for medical equipment no SFC event should be allowed to lead to such dangerous situations, i.e. at least two means of protection is required. One applicable safety standard is the IEC 60601 which is a series of technical standards for the safety and effectiveness of medical electrical equipment, published by the International Electrotechnical Commission.

Figure 2:
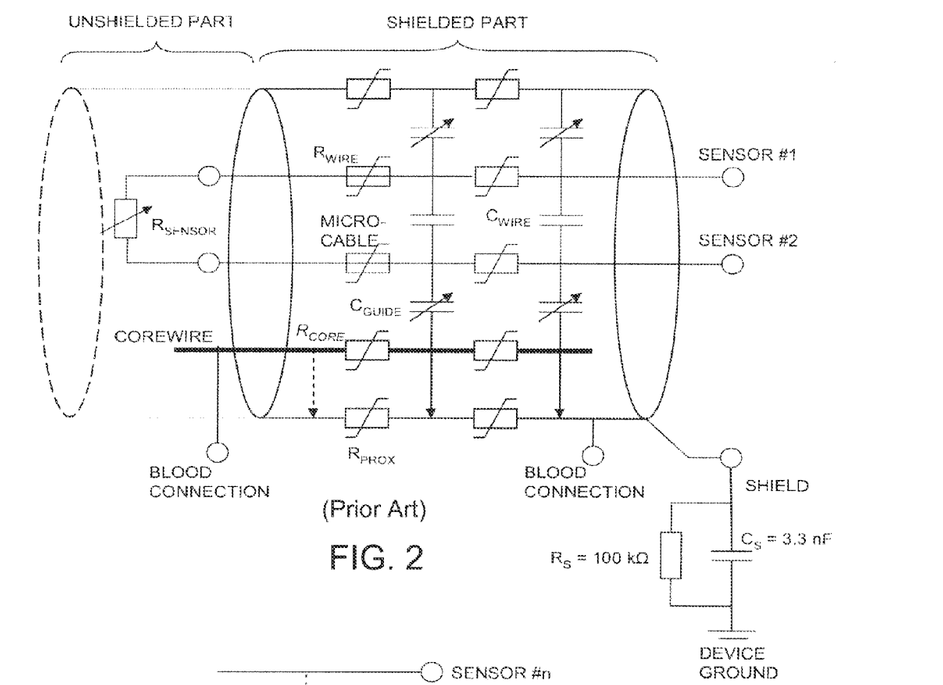
FIG. 2 is a schematic illustration of a passive current-limited shielding in connection with a sensor guide wire.

A passive current-limited shielding that traditionally has been used provides the added means of protection for electrical safety essentially comprising an impedance (e.g., a resistor) connected to device ground. This type of shielding is schematically illustrated in FIG. 2 in connection with a sensor guide wire. The shielding is achieved by a passive impedance connected between a shielded outer tubing of the guide wire and device ground. However the shielding provided is very modest, and at low frequencies (<10 kHz) largely ineffective. This makes the sensor measurements highly vulnerable to 50/60 Hz line voltage interference.

Figure 3:
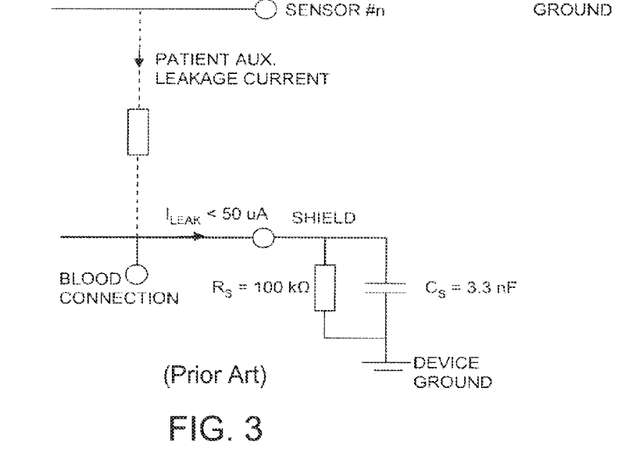
FIG. 3 is a schematic illustration of a passive type of shielding.

FIG. 3 is a schematic simplified circuit of the shielding in FIG. 2 illustrating passive current-limited shielding provided with an impedance circuit having a resistance Rs of 100 kΩ and a capacitance of 3.3 nF resulting in an impedance of approximately 91 kΩ at 50 Hz. The sensor voltage is less than 5 Volt, which results in a leakage current of less than 50 μA in order to fulfil the type "CF" SFC requirement.

SUMMARY

One object of the present invention is to achieve an improved shielding of a medical device, and in particular of intra-body sensors, that in particular effectively shields the sensor from both external and intra-body interference sources.

The disclosed invention may significantly reduce electrical interference for precision intra-body sensor measurements (pressure, temperature, flow, pH, position, etc.) by driving the patient body through a low-impedance connection (i.e., a direct connection to the bloodstream) with an electrical signal that counters and nulls out impinging electrical noise, while still complying with the highest level of electrical safety (type CF) through limited patient currents during normal and single-mode fault (SFC) conditions.

By using a current-limited active feedback network, the shield, or parts of a medical sensor that come in direct connection with the bloodstream of a patient, is actively driven by a small current to balance and effectively null out any voltage potential induced on the body of the patient by other interfering electrical equipment, both external (50/60 Hz line voltage, X-ray power supplies, ECG lead detection circuitry, etc.) and intra-body (pacemakers, implantable cardioverter-defibrillators (ICD), neurostimulators, RF ablation devices, ultrasound catheters, etc.), thus greatly reducing interference to precision measurements.

In further embodiments of the active noise cancellation device and method, internal sensor leakage currents, sensor settling times during switched operation, and motional artefacts due to cable capacitance variations of the sensor cables may also be reduced.

The embodiments disclosed herein may provide one or more of the following advantages:

1) Provides an active interference-noise cancellation through the use of feedback, by actively driving the patient body with a small correction current, thus using the patient body as a shield.

2) Fulfils patient leakage current requirements.

3) Allows the reference signal to be a fixed reference voltage or any sensor node signal. The reference signal may also be switched in time between different sensor signals.

4) When the reference signal is chosen as a sensor node signal it also suppresses motional artefacts due to cable capacitance variations (e.g., bending of sensor wire or catheter, organ movements, etc.) and errors due to sensor leakage currents.

5) Provides a means of detecting the interference frequency (e.g., 50/60 Hz) and detection and reduction of sensor leakage currents.

6) Provides an active shielding, supplied by an on-chip sensor active circuitry.

7) Provides an active shielding for multiple sensor nodes.

8) Speeds up sensor settling times when used in a switched or multiplexed technique.

9) Active noise cancellation may be performed by an external measurement device or directly on the sensor chip using active circuitry.

A further object is to provide a more reliable medical device by using the active noise cancellation device.

According to a first aspect of the present invention, there is provided a noise cancellation device comprising a low-impedance body connection electrode, arranged to actively apply a limited current to the patient's body, thereby using the patient's body as an active shield.

According to a second aspect of the present invention, there is provided a method comprising the steps of actively applying a limited current to the patient's body through a low-impedance connection, thereby using the patient's body as an active shield.

BRIEF DESCRIPTION OF THE DRAWINGS

The disclosure will become more fully understood from the following detailed description, taken in conjunction with the accompanying Figures, wherein like reference numerals refer to like elements, in which.

DETAILED DESCRIPTION

Before turning to the Figures, which illustrate exemplary embodiments in detail, it should be understood that the application is not limited to the details or methodology set forth in the description or illustrated in the Figures. It should also be understood that the terminology is for the purpose of description only and should not be regarded as limiting.

In one embodiment, an active noise cancellation device 2 for a medical device comprises an active circuit having a first input connection 8, a second input connection 10, and an output connection 12, a low-impedance body connection electrode 4 adapted to be in electrical contact with the bloodstream of a subject (e.g., a human or animal body), and a feedback branch 14 connecting said output connection 12 with said first input connection 8.

Figure 5:
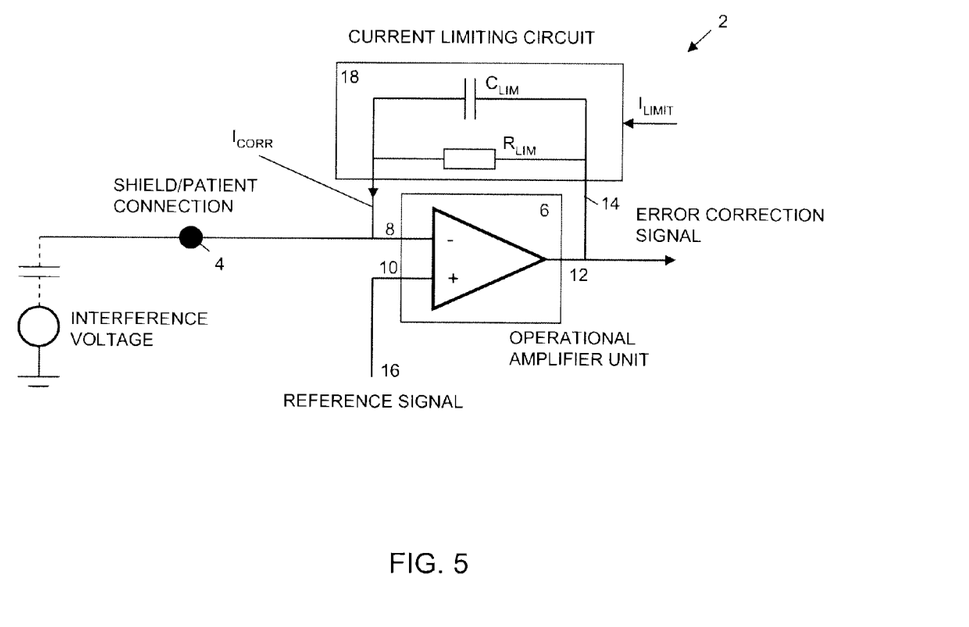
FIG. 5 is a schematic illustration of one embodiment of an active noise cancellation device according to an exemplary embodiment of the present invention.

Referring to FIG. 5, a basic principle of one embodiment of the active noise cancellation device is that a current limiting circuit 18, in the feedback branch 14, feedbacks an error correction current to the patient's body that counterbalances the influences from noise and interference voltage of the patient. In the embodiment of FIG. 5, the active circuit includes an operational amplifier unit 6 having a very high amplification. The operation amplifier unit 6 may be connected as a transimpedance amplifier or current to voltage (I-V) converter. The operational amplifier outputs an error correction voltage, causing an error correction current to flow through the current limiting circuit 18. The error correction current precisely counterbalances the interfering voltage at the negative input 8, thus keeping this input at the same potential as the reference input 10. The resistor $R_{LIM}$ both sets the I-V conversion factor and thus the output excursion of the operational amplifier for a given interference level, as well as limits the maximum DC correction current. Capacitor $C_{LIM}$ limits the AC correction current and provides frequency stabilization of the control loop.

The active noise cancellation device 2 is electrically connected to the patient via a low-impedance body connection electrode 4. The body connection electrode 4 is adapted to be in direct connection to the blood of the human or animal. The body connection electrode 4 may be in contact with the patient's blood by being located on an external portion of a medical device that is inserted into the patient's bloodstream. For example, if the medical device is a sensor guide wire, direct contact with blood can be achieved by connecting the body connection electrode 4 to an outer non-insulated tubing of the sensor guide wire that is in direct connection to the blood. When the medical device is inserted into a patient's body, the body connection electrode 4 is able to provide an electrical connection between the patient's body and the circuitry of the active noise cancellation device 2. As described in more detail below, the active noise cancellation device 2 acts to drive the patient's body to a desired potential, thereby cancelling any interference voltage (or current) within the patient's body.

Herein, low-impedance is generally meant impedance values less than 1 kΩ. The impedance value may be dependent on the material used in the body connection electrode 4. In various embodiments, the body connection electrode 4 has an impedance value of: less than 900Ω, less than 800Ω, less than 700Ω, less than 600Ω, less than 500Ω, less than 400Ω, less than 300Ω, or less than 200Ω. In another embodiment, the impedance value of the low-impedance body connection electrode 4 is in the interval of 10-100Ω.

Referring to FIG. 5, the body connection electrode 4 is connected to the first input connection 8 of an active circuit. The active circuit includes a first input connection 8, a second input connection 10, and an output connection 12. The active circuit may include an operational amplifier unit 6. In this embodiment, the predetermined reference signal 16 is connected to the second input connection 10 of the operational amplifier unit 6. The operational amplifier unit 6 acts to maintain the same voltage at each input terminal 8, 10. The presence of the feedback branch 14, which connects the output connection 12 of the operational amplifier unit 6 to the input connection 8, causes the operational amplifier unit 6 to output the voltage necessary to maintain the input terminals 8, 10 at the same potential. Thus, the operational amplifier unit 6 outputs an error correction signal (i.e., voltage) that will operate to bring the first input terminal 8 to the same voltage as the second input terminal 10, which is determined based on the reference signal 16. The error correction signal can also be used for other advantageous purposes, such as to measure the level of electrical interference on a patient, the capacitance of a sensor wire, and leakage current flowing through the patient or sensor.

The feedback branch 14 comprises a current limiting circuit 18 adapted to limit the error correction current through the feedback branch 14 such that it is lower than a predetermined current. As illustrated schematically in FIG. 4, the current limiting circuit 18 may generally have a designated transfer function H(s). The transfer function H(s) may be tailored to the specific medical device in which the active noise cancellation device 2 is applied. The transfer function H(s) may include any combination of circuit components that acts to limit the current flowing from the output connection 12 to the first input connection 8. Limiting the current flowing towards first input connection 8 also limits the current flowing to the body connection electrode 4 (i.e., to the patient's body). The ability of the current limiting circuit 18 to limit the current flowing to the patient's body is an important advantage of the active noise cancellation device 2. Conventional active shielding mechanisms pose risks to the patient because a leakage scenario could cause currents of a dangerous level to flow through the patient's body. However, the current limiting circuit 18 of the noise cancellation device 2 is configured to limit the current flowing through the patient's body, protecting the patient from dangerous current levels that might otherwise result from a mechanical failure of components during active shielding.

According to one embodiment, the error correction current (i.e., the current flowing from output connection 12 to input connection 8) is limited to be 50 μA or lower (such as 30 μA or 15 μA). The highest level of the error correction current may be related to applicable safety standards, such as the safety standard that was briefly discussed in the Background section. Furthermore, the active noise cancellation device may be in particular adapted to reduce the influence of an interference frequency of 50-60 Hz. In one embodiment, the current limiting circuit 18 includes an impedance circuit that is matched in relation to the highest allowable error correction current, and also to the frequencies of the noise and interference voltage.

In one embodiment, the current limiting circuit includes a resistor unit and a capacitance unit, as shown in FIG. 5. In this embodiment, $L_{LIMIT}$ is set by configuring $R_{LIM}$ and $C_{LIM}$ to have the desired resistance and capacitance, respectively, necessary to achieve a current limiting circuit 18 having the desired impedance. The desired impedance can also be achieved by alternative combinations of resistors, capacitors, or other circuit components.

Figure 4:
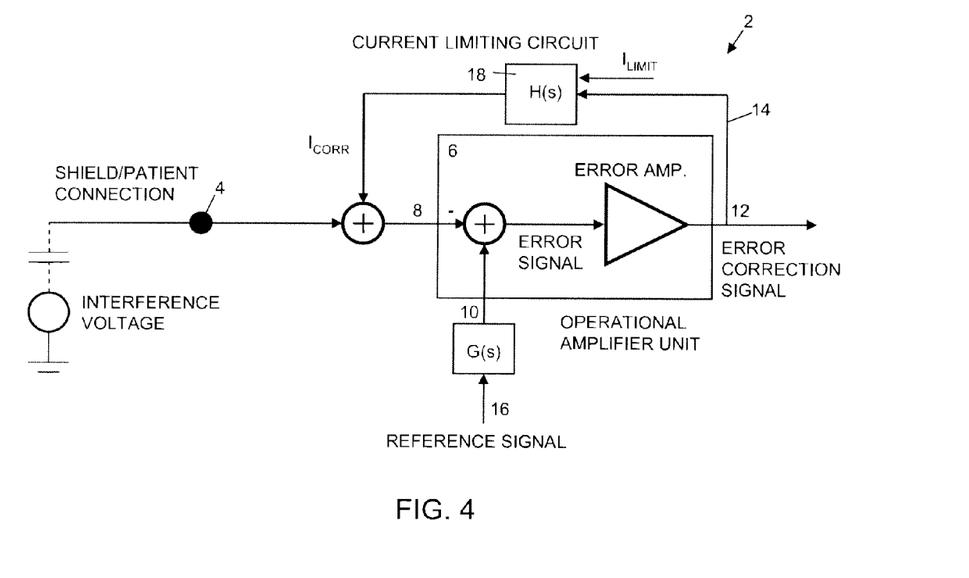
FIG. 4 is a schematic illustration of an active noise cancellation device according to an exemplary embodiment of the present invention.

As illustrated in FIG. 4 the reference signal 16 may generally have a designated transfer function G(s). The transfer function may be tailored for a particular frequency range and may also be chosen to ensure control loop stability to the specific medical device where the active noise cancellation device is applied. Maintaining control loop stability is important since the capacitive and/or resistive coupling from the patient body to the sensor signal may create a positive feedback path that could render the control loop unstable.

The predetermined reference signal 16 can be any stable voltage. Because the noise cancellation device 2 acts to bring the first input connection 8 to the same potential as the second input connection 10, it follows that the voltage at the body connection electrode 4 will be the same as the voltage at the second input connection 10. The noise cancellation device 2 therefore provides a mechanism to use the reference signal 16 to control the voltage at the body connection electrode 4, in effect cancelling out any interference voltage. According to one embodiment, the predetermined reference signal 16 is a fixed DC reference voltage related to a ground of the medical device.

According to another embodiment, the predetermined reference signal 16 is related to a sensor signal of said medical device. For example, the second input connection 10 may be connected to a microcable within the medical device (e.g., a microcable used for transmitting signals from a pressure sensor to the exterior of a patient). This embodiment provides an additional safety advantage of substantially preventing leakage currents from flowing from the medical device to the patient, even in the event of a mechanical failure of the medical device. This advantage occurs because when a sensor node is used as the reference signal 16, the noise cancellation device 2 causes the voltage of the patient (i.e., the voltage at the body connection electrode 4) to be the same as the voltage of the medical device (i.e., the voltage at the second input connection 10). Thus, even if the medical device were to experience mechanical failure, no leakage current would flow from the medical device to the patient. In this manner, the noise cancellation device 2 can be used to both: 1) limit the current flowing from the active noise cancellation device 2 to the patient (e.g., from output connection 12 to first input connection 8), and 2) prevent leakage current from flowing from the medical device to the patient in the event of a mechanical failure.

Using a sensor microcable as the reference signal 16 may speed up sensor settling times when a medical device is used in a switched or multiplexed technique. Each sensor microcable and tubing has associated distributed resistance, capacitance and inductance. The capacitance is typically around 100 pF/m of sensor wire. This capacitance creates an RC filter time constant. In other words, after energizing a particular sensor node, a certain time must pass before the voltages and currents have settled to their new values. This poses a fundamental limit as to how fast various sensor nodes can be switched between (such as temperature/pressure readout, etc.). By applying active shield drive to the tube and/or patient body using the active noise cancellation device 2, the effects of capacitance between a sensor cable (that is used as the reference signal 16 to the active drive) and the tube/patient body are essentially eliminated. Because the sensor cable and the tube/patient body are at the same potential, no current can flow, and therefore no RC time constant can be generated. Active drive using the noise cancellation device 2 thus greatly speeds up settling times.

When the reference signal is chosen as a sensor node signal it also suppresses motional artefacts due to cable capacitance variations (i.e. bending of sensor wire or catheter, organ movements etc.) and errors due to sensor leakage currents.

According to still another embodiment, the predetermined reference signal 16 is obtained by switching between different sensor signals of said medical device. This embodiment provides several advantages. First, the interference levels may be different on different sensor signals due to different associated impedances. Using the sensor signal that is to be measured at a given time as the reference signal 16 thus reduces interference particularly for that signal. Simply put, using a sensor signal as the reference signal 16 "protects" the signal that is to be measured at a given time. Second, using a certain sensor signal as a reference signal 16 reduces leakage current from that specific sensor signal when it is measured, allowing for a more stable and robust signal (the various sensor signals are typically at different voltages). Again, this embodiment provides the ability to "protect" the signal currently of interest. Third, the ability to switch between different sensor signals to obtain the reference signal 16 can be used to measure the leakage current from a specific sensor signal. For example, if a sensor has three signal leads, any leakage current can be pinpointed to a particular sensor lead.

According to one embodiment, the active noise cancellation device 2 is arranged at a distal end of a medical device. The medical device may be an elongated medical tube adapted to be inserted into a patient, such as a sensor guide wire provided with a pressure sensor at its distal end portion. The active noise cancellation device 2 may be arranged in connection with the pressure sensor by being integrated on the same chip. Similarly, if the medical device is a sensor guide wire provided with another type of sensor (e.g., temperature, flow, pH, etc.), the noise cancellation device 2 may be integrated on an alternative chip.

The present invention is thus applicable to any type of medical device provided with one or many intra-body sensor (s) arranged to measure, for example, one or many of pressure, temperature, flow, pH, or position of the sensor when the sensor is positioned at a distal tip portion of the medical device (so-called mGPS-sensors). The present invention can also be used in medical devices that are semi-permanently or permanently implanted into a subject.

Figure 6:
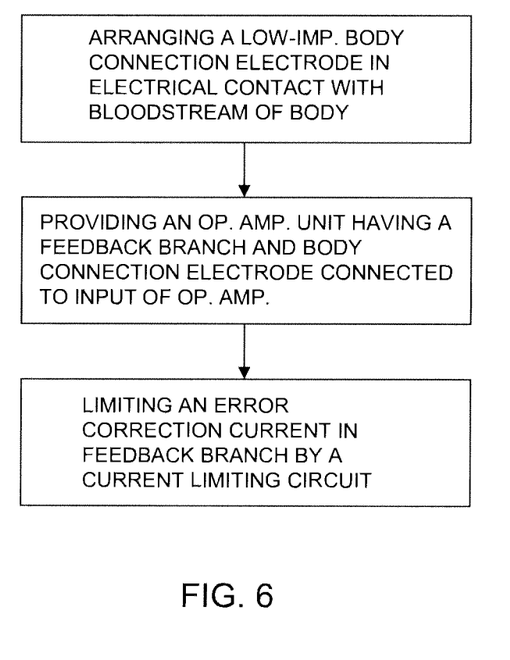
FIG. 6 is a method of active noise and interference cancellation according to an exemplary embodiment of the present invention.

A method of active noise and interference cancellation in a medical device will now be described with reference to the schematic flow diagram shown in FIG. 6.

In one embodiment, the method comprises providing an active circuit having a first input connection 8, a second input connection 10, and an output connection 12, wherein said second input connection is connected to a predetermined reference signal, arranging a low-impedance body connection electrode 4 in electrical contact with the bloodstream of a human or animal body, wherein said body connection electrode 4 is connected to said first input connection 8, and providing a feedback branch 14 connecting said output connection 12 with said first input connection 8. The method further comprises limiting an error correction current through said feedback branch 14 by providing a current limiting circuit 18 such that said error correction current is lower than a predetermined current. In the embodiment shown in FIG. 6, the step of providing an active circuit includes providing an operational amplifier unit having a feedback branch. The body connection electrode may be connected to an input of the operational amplifier unit.

The error correction current may be limited to be 50 μA or lower. The active cancellation may be in particular adapted to reduce the influence of an interference frequency of 50-60 Hz. As described above, the predetermined reference signal 16 may be a fixed reference voltage related to a ground of the medical device. Alternatively, the predetermined reference signal 16 may be related to a sensor signal of the medical device. In one embodiment, the reference signal 16 is obtained by switching between different sensor signals of the medical device.

The low-impedance body connection electrode 4 is adapted to be in direct connection to the blood of the human or animal. This is achieved in accordance with the different embodiments disclosed above in connection with the noise cancellation device 2.

In one embodiment, the current limiting circuit 18 includes an impedance circuit, including, for example, a resistor unit and/or a capacitance unit.

The construction and arrangement of the systems and methods as shown in the various exemplary embodiments are illustrative only. Although only a few embodiments have been described in detail in this disclosure, many modifications are possible (e.g., variations in sizes, components, and structures of the various elements, values of parameters, use of materials, etc.). For example, the position of elements may be varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. An active noise cancellation device for a medical device, comprising:
   an active circuit having a first input connection, a second input connection, and an output connection, wherein said second input connection is connected to at least one predetermined reference signal;
   a low-impedance body connection electrode adapted to be in electrical contact with a bloodstream of a subject, wherein the low-impedance body connection electrode is connected to said first input connection; and
   a feedback branch connecting the output connection with the first input connection;
   wherein said feedback branch comprises a current limiting circuit adapted to limit a current through said feedback branch to be lower than a predetermined current.

2. The active noise cancellation device according to claim 1, wherein said current is limited to be 50 µA or lower.

3. The active noise cancellation device according to claim 1, wherein said active noise cancellation device is adapted to reduce the influence of an interference frequency of 50-60 Hz.

4. The active noise cancellation device according to claim 1, wherein said at least one predetermined reference signal is a fixed reference voltage related to a ground of the medical device.

5. The active noise cancellation device according to claim 1, wherein said at least one predetermined reference signal is related to a sensor signal of said medical device.

6. The active noise cancellation device according to claim 1, wherein said at least one predetermined reference signal is obtained by switching between different sensor signals of said medical device.

7. The active noise cancellation device according to claim 1, wherein said body connection electrode is adapted to be in direct connection to the bloodstream of the subject.

8. The active noise cancellation device according to claim 1, wherein said current limiting circuit includes an impedance circuit.

9. The active noise cancellation device according to claim 1, wherein said current limiting circuit includes a resistor unit.

10. The active noise cancellation device according to claim 1, wherein said current limiting circuit includes a capacitance unit.

11. The active noise cancellation device according to claim 1, wherein said medical device is a sensor guide wire, and said body connection electrode is adapted to be connected to an outer non-insulated tubing of said sensor guide wire.

12. The active noise cancellation device according to claim 1, wherein said medical device is an elongated medical tube adapted to be inserted into the subject, and said noise cancellation device is arranged on a sensor chip at a distal end portion of said medical device.

13. The active noise cancellation device according to claim 12, wherein said elongated medical tube is a sensor guide wire provided with a pressure sensor at the distal end portion.

14. A sensor guide wire comprising the active noise cancellation device according to claim 1.

15. A method of active noise and interference cancellation in a medical device, comprising:
   providing an active circuit having a first input connection, a second input connection, and an output connection, wherein said second input connection is connected to at least one predetermined reference signal,
   arranging a low-impedance body connection electrode in electrical contact with a bloodstream of a subject, wherein said body connection electrode is connected to said first input connection,
   providing a feedback branch connecting said output connection with said first input connection, and
   limiting an error correction current through said feedback branch by providing a current limiting circuit such that said error correction current is lower than a predetermined current.

16. The method according to claim 15, wherein the step of providing an active circuit includes providing an operational amplifier unit.

17. The method according to claim 15, wherein said error correction current is limited to be 50 µA or lower.

18. The method according to claim 15, wherein said active noise and interference cancellation is adapted to reduce the influence of an interference frequency of 50-60 Hz.

19. The method according to claim 15, wherein said at least one predetermined reference signal is a fixed reference voltage related to a ground of the medical device.

20. The method according to claim 15, wherein said at least one predetermined reference signal is related to a sensor signal of said medical device.

21. The method according to claim 15, wherein said at least one predetermined reference signal is obtained by switching between different sensor signals of said medical device.

22. The method according to claim 15, wherein said body connection electrode is adapted to be in direct connection to the blood of the subject.

23. The method according to claim 15, wherein said current limiting circuit includes an impedance circuit.

24. The method according to claim 15, wherein said current limiting circuit includes a resistor unit.

25. The method according to claim 15, wherein said current limiting circuit includes a capacitance unit.

26. A medical device comprising:
   an active noise cancellation device comprising:
      an active circuit having a first input connection, a second input connection, and an output connection, wherein said second input connection is configured to be connected to at least one reference signal;
      a low-impedance body connection electrode adapted to be in electrical contact with a bloodstream of a subject, wherein the low-impedance body connection electrode is connected to said first input connection; and
      a feedback branch connecting the output connection with the first input connection;
      wherein said feedback branch comprises a current limiting circuit configured to limit a current through said feedback branch to be lower than a predetermined current.

* * * * *